United States Patent [19]

Roman, Jr. et al.

[11] Patent Number: 4,540,565

[45] Date of Patent: Sep. 10, 1985

[54] REDUCED IGG IN LOW IONIC STRENGTH MEDIUM FOR IMMUNOHEMATOLOGIC AGGLUTINATION

[75] Inventors: Daniel P. Roman, Jr.; Mitchell J. Fruitstone, both of Miami, Fla.

[73] Assignee: American Hospital Supply Corporation, Evanston, Ill.

[21] Appl. No.: 292,602

[22] Filed: Aug. 13, 1981

[51] Int. Cl.$^3$ .................... G01N 33/50; G01N 33/80
[52] U.S. Cl. .................................. 424/11; 436/520; 436/547; 436/826
[58] Field of Search .......................... 424/11, 12, 13; 436/520, 547, 826

[56] References Cited

U.S. PATENT DOCUMENTS 4,259,207  3/1981  Fruitstone ........................... 424/11
4,296,090  10/1981  Graham .............................. 424/11

OTHER PUBLICATIONS

Chan, P. C. Y. and Deutsch, H. F., "Immunochemical Studies of Human Serum Rh Agglutinins", *J. Immunol.*, 85:37, (1960).
Diamond, L. K., and Ableson, N. M., "The Detection of Rh Sensitization: Evaluation of Tests for RH Antibodies", J. Lab. Clin. Med., 30:68, (1945).
Diamond, L. K. and Denton, R. L., "Rh Agglutination in Various Media with Particular Reference to the Value of Albumin", J. Lab. Clin. Med., 30:821, (1945).
Freedman, J. et al., "Optimal Conditions for the Use of Sulphydryl Compounds in Dissociating Red Cell Antibodies", Vox. Sang., 30:231, (1976).
Knight, R. D., "Measuring IgG Anti-A/B Titres Using Dithiothreitol (DTT)", J. Clin. Path., 31:283, (1978).
Lincoln, P. J., and Dodd, B. E., "The Use of Low Ionic Strength Solution (LISS) in Elution Experiments and in Combination with Papin-Treated Cells for Titration . . . Antibody", Vox. Sang., 34:221-226, (1978).
B. Lowe and L. Messeter, "Antiglobulin Test in Low Ionic Strength Salt Solution for Rapid Antibody Screening and Cross-Matching", Vox. Sang., 26:53, (1974).
Okuno, T. and Kondelis, N., "Evaluation of Dithiothreitol (DTT) for Inactivation if IgM Antibodies", J. Clin. Path., 31: 1152, (1978).
Pirofsky, B. and Kordova, M. S., "Bivalent Nature of Incomplete Anti-D (Rho)", Nature, 197:392, (1963).
Pirofsky, B., and Rosner, E. R., "DTT Test: A New Method to Differentiate IgM and IgG Erytghrocyte Antibodies", Vox. Sang., 27:480, (1974).
Race, R. R., "An Incomplete Antibody in Human Serum", Nature, 153:771, (1944).
Romans, D. G. et al., "Conversion of Incomplete Antibodies to Direct Agglutinins by Mild Reduction: Evidence for Segmental Flexibility Within the Fc Fragment of Immunoglobulin G", Proc. Nat. Acad. Sc., 74: 253, (1977).
Wiener, A. S., "A New Test (Blocking Test) for Rh Sensitization", Proc. Soc. Expr. Biol. & Med. 56: 173, (1944).
Package insert for a Blood Grouping Serum marketed as Novasera.

*Primary Examiner*—Sidney Marantz
*Attorney, Agent, or Firm*—Bernard, Rothwell & Brown

[57] ABSTRACT

An antiserum for immunohematologic agglutination reactions involving IgG antibodies wherein reduced IgG antibodies are suspended in a low ionic strength medium.

29 Claims, No Drawings

REDUCED IGG IN LOW IONIC STRENGTH MEDIUM FOR IMMUNOHEMATOLOGIC AGGLUTINATION

BACKGROUND OF THE INVENTION

The present invention relates to a novel antiserum. More particularly, the invention relates to an antiserum for immunohematologic agglutination reactions involving IgG antibodies.

In blood typing and crossmatching procedures, erythrocytes are contacted with serums to determine the antigenic characteristics of the erythrocytes, the antibody composition of the serum, or the compatibility of patient and donor blood. Frequently, reagent erythrocytes or antiserums, whose antigenic or antibody content are known, are used to characterize patient serum or cells. In typing procedures, the antigenic composition of patient red cells is determined by contacting those cells with various antiserums, and reactivity is measured by observing whether or not the cells agglutinate. Agglutination is a positive reaction indicating the presence of antigens corresponding to antibodies contained in the antiserum employed in the reaction.

The antibodies employed in the major blood grouping procedures, e.g., for types A, B, O, and AB, are IgM antibodies. Such antibodies are thought to be polyvalent, and can cause direct cell agglutination in saline solution. Thus, these antibodies are variously referred to as complete antibodies, direct agglutinins and saline agglutinins. There are important antibodies of the IgG class, notably those employed in Rh typing, which are thought to be divalent and which directly agglutinate cells only weakly in saline, or not at all. Means have been devised for potentiating reactions involving IgG antibodies so that they will directly agglutinate cells having their corresponding antigens. A widely accepted potentiating technique is to employ albumin in the suspending medium in a relatively high concentration. Diamond, L. K., and Denton, R. L., *J. Lab. Clin. Med.*, 30, 821 (1945). This procedure is useful, especially when results are needed promptly, but it suffers from several disadvantages, the most important of which is that it sometimes causes agglutination of sensitized red cells (i.e., false positive tests).

Early investigators reported that IgG antibodies could be converted to direct agglutinins by chemical reduction. For instance, Chan, P. C. Y. and Deutsch, H. F., *J. Immunol.*, 85:37 (1960) reported that Rh antibodies of the IgG class could be converted to direct agglutinins by chemical reduction with 2-mercaptoethanol. This observation has been confirmed by subsequent investigators. For instance, Romans et al., *Proc. Nat. Acad. Sci.*, 74:2531 (1977) reported results of experiments in which unpurified antibodies in whole serum were reduced with 2-mercaptoethanol, dithioerythritol, and dithiothreitol to yield direct agglutinins. The Romans, et al. work focused on the Rh and Kell antigens.

Heretofore, the interest in chemically reduced antibodies has been largely academic. The procedure has been employed to differentiate IgG from IgM antibodies (IgM antibodies are destroyed by chemical reduction), but until recently, it has not been commercially employed for the preparation of blood grouping serums. The primary reason that the procedure has not been accepted commercially is that direct agglutinins resulting from chemical reduction have very weak reactivity and require lengthy incubation times. The reactivity of such antibodies has been observed to be inferior to that of the same antibodies which had not been chemically reduced, but merely potentiated with albumin.

SUMMARY OF THE INVENTION

In accordance with the present invention, an antiserum is disclosed which comprises an erythrocyte-agglutinating amount of a chemically reduced IgG antibody dissolved in a low ionic strength medium containing sufficient organic solute to provide an osmolality of from about 150 mOsm per kg. $H_2O$, to about 450 mOsm per kg. $H_2O$; sufficient salt of an alkali or alkaline earth metal to provide an ionic strength equivalent to about a 0.01 molar to about a 0.10 molar solution of sodium chloride; and a pH of from about 6.0 to about 8.0.

DETAILED DESCRIPTION OF THE INVENTION

The present invention resides in the discovery of the synergistic activity of a mixture of chemically reduced IgG antibodies in a low ionic strength solution. In U.S. Pat. No. 4,259,027 and copending U.S. patent application, Ser. No. 225,098 filed Jan. 14, 1981, entitled "Suspending Medium for Immunologic Reactions", (both of which are incorporated herein by reference), Fruitstone, et al. describe a low ionic strength diluent for use in conventional blood typing, grouping, crossmatching procedures and the like. It has been found that antiserums prepared by dissolving chemically reduced IgG antibodies in low ionic strength suspending mediums, particularly the mediums described in the above-referenced patent and patent application, have several distinct advantages over the prior art.

The antibodies employed in such antiserums are generally prepared by known procedures. Serums containing the antibodies of interest may be utilized in the unpurified state for the preparation of chemically reduced antibodies, or such antibodies may be purified, e.g., by ion exchange chromatography, prior to reduction. Generally, such serums are used in the unpurified state and are obtained from pools of serum from human donors known to possess the antibody of interest.

The present invention is generally applicable to antibodies of the IgG class, which includes antibodies to Rh antigens such as anti-D, anti-C, anti-E, anti-c, and anti-e as well as other IgG antibodies, such as those to antigens of the Lutheran, Kell, Duffy, Kidd or MNS blood groups. IgM antibodies are destroyed by the reduction procedures described herein, thus that procedure is at least partially effective for removing those antibodies and purifying the serum with respect to the IgG antibodies.

Chemical reduction of the antibodies is advantageously accomplished by reaction with a disulfide reducing compound. Any such compound may be employed which does not deleteriously affect the desired IgG antibody. Preferred disulfide reducing compounds are thioalcohols, including mercaptans, e.g., 1,3-dimercaptopropan-2-ol, 2,3-dimercaptopropanol, 1,2-dimercaptoethane, dithiothreitol, dithioerythritol, and mercaptoethanol, L-thiazolidine-4-carboxylic acid as well as amionethylisothiouronium bromide. Particularly preferred reducing compounds are mercaptoethanol, dithioerythritol, and dithiothreitol.

The reducing compound may be added to the serum in a reducing amount, and the serum incubated under antibody-reducing conditions for a period of time sufficient to effect substantial reduction of the IgG antibodies. Generally, incubation of the serum at about room temperature for about 30–90 minutes has been found effective. The amount of reducing compound used is not critical, provided that sufficient material is present to reduce substantially all of the IgG antibodies. The concentration of the reducing compound generally ranges of from about 0.001–0.25 mmoles of reducing compound per ml. serum, preferably from about 0.01–0.1 mmoles of reducing compound per ml. of serum. After reaction of the serum with the reducing compound, the serum may be purified by dialysis, if desired. Such purification has not been found necessary and is generally omitted.

Reduction results in cleavage of disulfide bonds of the antibody to form free sulfhydryl groups. These free sulfhydryl groups can recombine under oxidizing conditions, and to prevent such recombination, an alkylating amount of an alkylating agent is advantageously added to the serum. Alkylation of the sulfhydryl groups inhibits their recombination. Any effective alkylating agent, such as iodoacetamide or iodoacetic acid may be employed in a preserving amount. Generally, 0.002–0.5 mmoles of alkylating agent per ml. of serum is used.

The chemically reduced antibodies are dissolved in a low ionic strength medium. When unpurified serum is used as the starting material, the reduced and alkylated serum may simply be diluted in the low ionic strength medium. The ratio of serum to low ionic strength medium will vary, depending upon the concentration of antibodies in the original serum and the desired titer of the final antiserum product. If the antibody concentration in the original serum is too low, the antibodies may be concentrated by methods well known in the art prior to addition to the low ionic strength medium. Conversely, if the antibody concentration is too high, the serum may be diluted with physiologic saline to achieve the desired level of reactivity when added to the low ionic strength medium. Generally, a volume ratio of serum concentrated, undilute, or diluted with saline to low ionic strength medium of from about 0.5:10 to about 3:10, preferably from about 1:10 to about 2:10 has been found to provide useful reaction strengths. The antiserum may be clarified and sterilized, e.g., by sterile filtration, prior to packaging.

The low ionic strength medium employed in this invention has an ionic strength equivalent to about a 0.01 molar to about a 0.10 molar solution of sodium chloride. The solution advantageously contains gelatin, and preferably contains both gelatin and albumin. A particularly preferred low ionic strength salt solution is described in Example I below.

When gelatin is included in the low ionic strength medium, the amount of gelatin added will depend in part on the gel strength (Bloom rating) of the gelatin used. The higher the Bloom rating, the lower the gelatin concentration can be. Gelatins having Bloom ratings from about 75 to about 300 are generally employed and Bloom ratings from about 100 to about 275 are preferred. For 100 Bloom gelatin, the concentration generally ranges from about 0.5 weight percent to about 1.5 weight percent, preferably from about 0.7 weight percent to about 1.3 weight percent. Gelatin having a Bloom rating of 260 is employed at a concentration of from about 0.2 weight percent to about 0.6 weight percent, preferably from about 0.25 weight percent to about 0.5 weight percent and most preferably about 0.3 weight percent. The relationship between Bloom rating and concentration may conveniently be expressed as the arithmetic product of the two factors. Thus, the Bloom rating times concentration (in weight percent) generally ranges from about 40 to about 150, preferably from about 40 to about 130 and most preferably from about 45 to about 90. Solutions in which the Bloom rating-concentration product is lower than about 40 have been found to result in a significant reduction in serologic activity of the resulting antiserum, and Bloom rating-concentration products greater than about 150 may cause gelling of the product at room temperature.

The gelatin used in this invention is advantageously finely divided to facilitate dissolution, and is preferably of at least laboratory grade purity in accordance with the listing in the U.S. Pharmacopea or National Formulary. The source of the gelatin and the procedures used in its preparation are conventional. Thus, gelatin obtained from the partial hydrolysis of collagen derived from calfskin, pigskin, and the skin, white connective tissue, and bones of various animals all appear suitable. Similarly, the gelatin may be derived from an acid-treated precursor or from an alkali-treated precursor.

Albumin is also advantageously dissolved in the solution at a concentration of from about 3.0 weight percent to about 7.0 weight percent, preferably from about 4.0 weight percent to about 6.0 weight percent. The source of the albumin used is not critical. Bovine serum albumin is preferred, because of its availability and cost, but albumin obtained from the fractionation of plasma from virtually any animal, such as horse, sheep, swine, chicken and human, may be employed. The albumin is preferably substantially salt-free or low in salt, so as not to contribute appreciably to the ionic strength of the final solution. The effect of the salt concentration of the albumin on ionic strength should be considered when determining the concentration of other ingredients.

Because the ionic strength of the medium employed in the present invention is lower than that of physiological saline, the osmolality is adjusted to approximate physiological values. If the osmolality of the solution is too low, erythrocytes suspended in the solution will lyse, and if it is too high, they will become crenated. The osmolality of the solution is controlled within a range of from about 150 mOsm/kg. $H_2O$ to about 450 mOsm/kg. $H_2O$. Preferably, the osmolality is adjusted from about 250 mOsm/kg. $H_2O$ to about 400 mOsm/kg. $H_2O$. Any solute which does not substantially increase the ionic strength of the medium, and which does not deleteriously react with any other components of the solution or interfere with the immunologic reaction may be employed to control osmolality. Such solute is preferably an organic compound, such as an amino acid, a sugar, a soluble alcohol, etc. Particularly preferred solutes are glycine, sucrose, and glucose.

The pH of the antiserum of this invention is preferably conducive to immunohematologic reactions. Accordingly, the pH of the low ionic strength solution is advantageously adjusted from about 6.0 to about 8.0. A preferred pH range is from about 6.4 to about 7.4. The pH may be adjusted with an acid or a base as is well known in the art. Mineral acids such as hydrochloric acid, sulfuric acid, and the like and alkali or alkaline earth metal hydroxides such as sodium hydroxide, potassium hydroxide, etc. are used. To provide greater control of pH, a suitable buffer may be used in a pH-controlling amount. Any buffer capable of controlling pH within the desired range and which does not interfere with the reaction, may be employed. Conventional phosphate buffers are preferred for this purpose.

The ingredients of the low ionic strength medium may be combined in any convenient manner. A preferred manner of preparing the solution is to sequentially dissolve the ingredients in a portion of the total volume of water to be used. The water may be heated, e.g., to 50° C.–60° C. and stirred to facilitate dissolution of the gelatin (if added). After the gelatin is dissolved, the remaining ingredients are dissolved in the solution. The pH is then adjusted and the remaining water is added.

Chemically reduced IgG antibodies are dissolved in the low ionic strength medium, to form an antiserum in accordance with this invention. The addition of the reduced antibodies to the low ionic strength medium may be accomplished in a conventional manner.

The antiserum will usually be packaged and stored for extended periods of time; therefore, it is desirable to sterilize the solution and to incorporate a preservative therein. Sterilization may be accomplished by conventional means, e.g., sterile filtration, and suitable preservatives include bacteriostats or antibiotics such as preserving amounts of thimerosal, phenylmercuric acetate, sodium azide, neomycin or chloramphenicol, or combinations thereof.

The antiserums of the present invention may be used in the same manner as conventional blood grouping serums. Such antiserums may be employed in direct agglutination reactions using either slide or test tube techniques. Although definitive agglutination reactions are generally obtained, cells which have been reacted with the antiserums may be subjected to antiglobulin testing also if desired. The antiserums of this invention have been found to provide stronger agglutination reaction results at lower temperatures than high protein serums containing unreduced antibodies. Thus, the reactions are usually conducted at room temperature, rather than at an elevated temperature.

This invention has been found to provide antibodies which permit reduced incubation times, permit reactions at room temperature, provide strong agglutination reactions, obviate the necessity for using the relatively rare saline antiserums, virtually eliminate the probability of non-specificity caused by residual contaminating trace anti-A or anti-B IgM isoagglutinins, and in some cases may eliminate the necessity of antiglobulin testing.

The invention is further illustrated by the following examples, which are not intended to be limiting.

EXAMPLE I

A batch of low ionic strength medium (LISM) was prepared as follows: Approximately 400 kg. of purified water was charged into a stainless steel tank equipped with an agitator and a heating means. The water was heated to 50° C.–60° C. Gelatin (8.0 kg.) having a Bloom rating of 100, was added to the water and the mixture was stirred for 2 to 2.5 hours at 50° C.–60° C. The temperature was maintained while albumin (343 kg. of 15% solution), sodium chloride (716 g.), glycine (21.6 kg.), sodium phosphate dibasic (85 g.), sodium phosphate monobasic (83 g.), and thimerosal (100 g.) were dissolved therein. The pH of the solution was adjusted to 6.9±0.1 with 1N sodium hydroxide, and water was added to a final weight of 1019 kg. The solution was sterile filtered while hot and filled into bottles. The filled bottles were stored at room temperature.

Samples of human serum or defibrinated plasma containing antibody to the D ($Rh_o$) blood group antigen were screened for appropriate specificity and potency using techniques well known in the art. Samples having acceptable specificity (possessing only anti-D or also containing either anti-A or anti-B or both) and potency (met or exceeded the minimum titer specification in comparison with U.S. Bureau of Biologics reference serum) were treated by chemical reduction followed by alkylation. For each 1000 ml. of serum, 1.54 g. of dithiothreitol was added as a disulfide reducing agent. The solution was allowed to mix and incubate at room temperature for 1 hour. Then alkylation was accomplished by adding 4.6 g. iodoacetamide for each 1000 ml. of original serum. The solution containing the iodoacetamide was then allowed to mix and incubate at room temperature for 1 hour. At the end of that incubation time, the solution was stored at 2° C.–8° C. Each reduced and alkylated serum was then re-evaluated for specificity and potency as above. Samples acceptable by the criteria described above, and for which any anti-A or anti-B remaining after the reduction and alkylation could be neutralized by the addition of a small amount of blood group substance A or B, were then pooled to make the antiserum "base". The base was filtered to remove particulate matter and then passed through a series of membrane filters to further clarify the pool.

Specificity and potency testing was then performed on the base as described in the preceeding paragraph for individual bleeds, except that, to prevent non-specificity caused by higher anti-A or anti-B titers, the base could not have anti-A or anti-B titers greater than 1:4 when tested using licensed antiglobulin serum. From these experiments, it was determined that a 1:8 dilution of the base in the low ionic strength medium described in the first paragraph of this example would have the characteristics desired for the antiserum. Therefore, 1000 ml. of base were added to 7000 ml. of the low ionic strength medium. The resulting mixture was then sterile filtered and filled into vials.

EXAMPLE II

The procedure of Example I is repeated in all essential details except that a base is prepared having sufficient potency that it may be used at a final concentration of 1:32. This high titered base (250 ml.) and 750 ml. of physiologic saline may be substituted for the 1000 ml. of the lower titered base of Example I. This procedure will result in an antiserum having serological characteristics indistinguishable from those of the antiserum prepared in Example I.

EXAMPLE III

The procedure of Example I was repeated in all essential details except that antibody samples acceptable in terms of specificity and potency were pooled to make a base prior to reduction and alkylation. This method resulted in an anti-D serum having characteristics indistinguishable from those of the antiserum prepared in Example I.

EXMPLE IV

The procedure of Example I was repeated in all essential details except that the preservative was changed from thimerosal to sodium azide. To accomplish this, 796 g. sodium azide was substituted for the 716 g. of sodium chloride and the thimerosal was deleted from the formulation. This procedure resulted in an antiserum serologically indistinguishable from the antiserum prepared in Example I.

EXAMPLE V

The anti-D serum described in Example III was tested by 5 blood bank laboratories in over 3000 tests involving over 400 blood samples from known D ($Rh_o$) positive individuals and a suitably large number of controls lacking the D ($Rh_o$) antigen. These tests were designed to confirm the efficacy of the antiserum in comparison with the standard high protein anti-D reagent currently employed by most blood banks. Cells for testing were obtained from normal blood donors or from patient samples routinely submitted to the laboratory. No selection of a patient population was made by age, sex, medication, disease state, etc.

Laboratories 1 and 2 performed both tube and slde tests on each sample. For the tube tests, 2–5% red cell suspensions in saline and in autologous serum or plasma were prepared. One drop of each cell suspension was tested with both one and two drops of antiserum. In addition, 2–5% cell suspensions were tested by adding cells adhering to the tip of an applicator stick to the antiserum. Each tube test was read following immediate centrifugation (IS) of the cell-serum mixture. Testing for the $D^u$ antigen (a weak variant of the D antigen) was performed on known $D^u$ positive cells by incubating those tubes at room temperature for 30 minutes and converting them to antiglobulin phase.

For the slide test, two drops of a 40–50% red cell suspension in autologous serum or plasma were placed on a glass microscope slide and one drop of antiserum was added between the two drops of cells. The slide was placed on a warm viewbox (40° C.–50° C.) and the cells were then mixed with the antiserum. Time of appearance of agglutination and the reaction strength at the end of two minutes were recorded.

In addition to the tests employing the experimental anti-D serum, parallel tests were performed on the same samples using a high protein anti-D serum prepared from an aliquot of the same anti-D base pool taken prior to the reduction and alkylation of Example III. This untreated base was used at a final dilution of 1:6 since its reactivity in albumin was less than its reactivity in the low ionic strength medium.

Laboratories 3, 4 and 5 performed tube tests on random samples coming through their laboratories using the experimental formulation in comparison with the licensed anti-D serum (various manufacturers) which they routinely employed in their laboratories. Each investigator selected from among the many test variations described in the preceeding paragraphs that test method which most closely corresponded to the method for the commercial anti-D blood grouping serum routinely employed. Each then performed parallel testing with both the commercial and experimental anti-D reagents and their Rh-hr controls. Throughout the testing, Rh-hr control serums (which were identical in composition to each reagent antiserum but lacked the anti-D activity) were used to detect rare, non-specific reactions.

All reactions were observed using some kind of optical aid such an agglutination viewer or lighted viewbox. The reactions were read macroscopically and graded as follows:

1. Grading System - Tube Typings:
   4+ = One large button that remains intact on gentle resuspension.
   3+ = Several large agglutinates on gentle resuspension.
   2+ = Many small agglutinates of approximately equal size, clear background.
   1+ = Many small but definite agglutinates, finely granular appearance, opaque reddish background.
   ± = Minute agglutinates, many unagglutinated cells.
   h = Hemolysis.
   0 = Negative reaction. No agglutination or hemolysis.
2. Grading System - Slide Typings:
   4+ = One solid clump or 2–4 large agglutinates with a clear background.
   3+ = Many large, medium and small agglutinates with a clear background.
   2+ = Uniform medium size agglutinates with a small amount of unagglutinated cells in the background.
   1+ = Many small agglutinates with many unagglutinated cells in the background.
   ± = Minute agglutinates with a background of mostly unagglutinated cells.
   0 = Negative reaction. A homogeneous suspension of unagglutinated cells.

The results of these tests were reported and grouped according to each type or test. The data was summarized and statistical analyses were performed on the comparisons. This analysis applies only to the blood samples positive at immediate centrifugation, not to $D^u$'s (insufficient number of samples) or negatives.

The performance of the anti-D serum of the present invention in the testing performed in Laboratories 1 and 2 is compared to the corresponding high protein anti-D serum in Table I. The data clearly show that the experimental antiserum performed equal to or significantly better than the high protein formulation in most variations of the test procedures.

Table II summarizes the results of the tube testing in Laboratories 3, 4 and 5 using 4 different lots of commercial high protein anti-D serum (from 2 manufacturers) in comparison with the experimental reduced and alkylated anti-D serum. From these data, it was statistically determined that in testing in Laboratory 3 the high protein reagent was slightly better than the experimental reagent, in Laboratory 4 no difference was observed, and in Laboratory 5 the experimental reagent performed slightly better than the control high protein reagent. Overall, there appeared to be very little difference in the performance of the two types of reagents in this tube testing.

TABLE I

| Test Type | Anti-coagulant | Observed Differences/ Number Tests | Experimental Anti-D Serum Better at $P \leq 0.01$ | High Protein Anti-D Serum Better at $P \leq 0.01$ | No Statistical Difference at $P \leq 0.01$ |
|---|---|---|---|---|---|
| Stick | None | 62/100 | | X | |
| | EDTA | 44/100 | | | X |
| | CPD | 61/92 | | X | |

TABLE I-continued

| Test Type | Anti-coagulant | Observed Differences/ Number Tests | Experimental Anti-D Serum Better at P ≦ 0.01 | High Protein Anti-D Serum Better at P ≦ 0.01 | No Statistical Difference at P ≦ 0.01 |
|---|---|---|---|---|---|
| | CPDA-1 | 59/92 | | X | |
| Tube - | None | 52/100 | X | | |
| 1 drop | EDTA | 40/100 | | | X |
| Saline | CPD | 49/92 | | X | |
| Suspension | CPDA-1 | 47/92 | | X | |
| Tube - | None | 59/100 | X | | |
| 2 drops | EDTA | 61/100 | X | | |
| Saline | CPD | 39/92 | | | X |
| Suspension | CPDA-1 | 42/92 | | | X |
| Tube - | None | 60/100 | X | | |
| 1 drop | EDTA | 48/100 | X | | |
| Plasma | CPD | 37/92 | | | X |
| Suspension | CPDA-1 | 42/92 | | | X |
| Tube - | None | 70/100 | X | | |
| 2 drops | EDTA | 58/100 | X | | |
| Plasma | CPD | 34/92 | X | | |
| Suspension | CPDA-1 | 36/92 | X | | |
| Slide - | None | 83/100 | X | | |
| Time to | EDTA | 73/100 | X | | |
| Appearance | CPD | 83/92 | X | | |
| | CPDA-1 | 84/92 | X | | |
| Slide - | None | 69/100 | | X | |
| Strength at | EDTA | 46/100 | | X | |
| Completion | CPD | 83/92 | | X | |
| | CPDA-1 | 80/92 | | X | |

TABLE II

| | Experimental Anti-D Serum | High Protein Anti-D Serum |
|---|---|---|
| Laboratory 3 Tube Tests vs. commercial high protein Anti-D Serum (Lots A and B) from Manufacturer No. 1 | | |
| 55 differences observed/ 182 tests High protein better at p = 0.01 | | |
| Mean of reaction scores | 3.3 | 3.4 |
| Percent of reactions greater than 2+* | 98 | 97 |
| Laboratory 4 Tube Tests vs. commercial high protein Anti-D Serum (Lot C) from Manufacturer No. 2 | | |
| 63 differences observed/ 200 tests No statistical difference at p = 0.05 | | |
| Mean of reaction scores | 3.4 | 3.4 |
| Percent of reactions greater than 2+* | 99 | 100 |
| Laboratory 5 Tube Tests vs. commercial high protein Anti-D Serum (Lot D) from Manufacturer No. 1 | | |
| 14 differences observed/ 51 tests Experimental Anti-D better at p = 0.02 | | |
| Mean of reaction scores | 3.3 | 3.1 |
| Percent of reactions greater than 2+* | 100 | 96 |

*A 2+ reaction is the minimum generally accepted as being unquestionably positive for a reagent blood grouping serum.

EXAMPLE VI

The procedure of Example I was repeated in all essential details except reduced and alkylated bases of other specificities were substituted at a 1:8 dilution for the anti-D base of Example I. This procedure resulted in a potentiation of the IgG antibodies to the specific red cell antigens as had been seen previously with the anti-D.

Table III summarizes these results. The data presented are the agglutination titers (2-fold dilutions) obtained after 1 hour incubation. The untreated base was initially diluted 1:8 in physiologic saline, albumin or low ionic strengh medium and then further diluted in the same diluent. These titrations were compared with a corresponding series of dilutions of reduced and alkylated base in the low ionic strength medium. After the 1 hour incubation period, tests for some of the antibodies were converted to antiglobulin phase to attempt to detect IgG which had been bound but not in sufficient quantity to cause agglutination. The table shows that the three reduced and alkylated Rh blood group antibodies (anti-C, -c̄, and -E) were potentiated in a manner similar to that of the anti-D described in the preceeding examples. The reduced and alkylated anti-s̄, previously detectable only at antiglobulin phase, was converted to a potent room temperature agglutinin. The reduced and alkylated anti-Kell, while not potentiated enough to show reactivity at room temperature, as well as the treated anti-s̄, showed significantly enhanced binding as evidenced by the antiglobulin reaction. Thus, the reduction and alkylation procedure, coupled with dilution in low ionic strength medium, has been shown to be effective in potentiating the activity of antibodies of several blood groups. These data further indicated that, in general, the potentiating activity was equivalent to or better than that obtained with high protein media currently in use.

TABLE III

| Base | Anti-s | | | Anti-K | | | Anti-C | | | Anti-c̄ | | |
|---|---|---|---|---|---|---|---|---|---|---|---|---|
| Diluent | Sal | LISM | LISM | Sal | LISM | LISM | Alb | LISM | LISM | Alb | LISM | LISM |
| Treatment | None | None | R & A | None | None | R & A | None | None | R & A | None | None | R & A |
| Incubation | 37° C. | RT | RT | 37° C. | RT | RT | 37° C. | RT | RT | 37° C. | RT | RT |
| | 1 hr | 1 hr | 1 hr | 1 hr | 1 hr | 1 hr | 1 hr | 1 hr | 1 hr | 1 hr | 1 hr | 1 hr |
| Titer* | <1 | <1 | 8+ | <1 | 4+ | <1 | 4 | 8 | 4 | 16+ | 16 | 16+ |
| Antiglobulin* | 16 | NT | 128+ | 16+ | NT | 128+ | NT | NT | NT | NT | NT | NT |

Sal = Physiologic saline.
LISM = Low ionic strength medium of Example I.
Alb = 20% bovine albumin.
R & A = Reduced and alkylated.
NT = Not tested.
*Reciprocal of the highest dilution giving at least a 1+ reaction. A "+" sign following the titer value indicates that one or more additional dilutions gave weak positive (less than 1+) reactions. Titer differences greater than 2-fold are considered significant.

EXAMPLE VII

In this experiment, antibody samples were reduced and alkylated and subjected to 2-fold serial dilutions in physiologic saline, 22% bovine albumin, the low ionic strength solution (LISS) of Low and Messeter (Vox Sang. 26, 53–61 (1947)) and the low ionic strength medium (LISM) described in Example I. Incubations were carried out at the optimum temperatures and times for reactions in the various diluents. After incubation, each test was converted to antiglobulin phase using monospecific anti-IgG reagents. Simultaneously, aliquots of the same serum that had not been reduced and alkylated were tested in parallel by identical methods.

Table IV presents the results of these tests with 3 antibodies of the Rh-hr blood group system. The data in this table show that in virtually all cases except for tests incubated in albumin, when examined by immediate centrifugation or after incubation at room temperature or 37° C., the reduced and alkylated antibody gave significantly higher titers than the corresponding untreated antibody. These differences were not observed at the antiglobulin phase, however, indicating that the untreated antibody had attached to the red cells just as well as the reduced and alkylated antibody but was unable to readily cause direct agglutination except in the albumin medium.

TABLE IV

Anti-D

| | Physiologic Saline | | | | | | Albumin | | | | | |
|---|---|---|---|---|---|---|---|---|---|---|---|---|
| Diluent Test Phase | Immediate Centrifugation | | 15' Incubation Room Temp. | | Anti-IgG Serum | | Immediate Centrifugation | | 30' Incubation 37° C. | | Anti-IgG Serum | |
| Treatment | None | R & A | None | R & A | None | R & A | None | R & A | None | R & A | None | R & A |
| Titer* | 1 | 32+ | <1 | 256 | 512+ | 512+ | 128 | 64+ | 2048 | 512+ | 2048 | 2048 |

| | Low Ionic Strength Solution (LISS) of Low and Messeter | | | | | | | | | | | |
|---|---|---|---|---|---|---|---|---|---|---|---|---|
| Diluent Test Phase | Immediate Centrifugation | | 10' Incubation Room Temp. | | Anti-IgG Serum | | Immediate Centrifugation | | 15' Incubation 37° C. | | Anti-IgG Serum | |
| Treatment | None | R & A | None | R & A | None | R & A | None | R & A | None | R & A | None | R & A |
| Titer* | <1 | 256+ | <1 | 512+ | 4096 | 1024+ | <1 | 256+ | <1 | 512+ | 2048+ | 2048+ |

| | Low Ionic Strength Medium (LISM) of Example I | | | | | | | | | | | |
|---|---|---|---|---|---|---|---|---|---|---|---|---|
| Diluent Test Phase | Immediate Centrifugation | | 10' Incubation Room Temp. | | Anti-IgG Serum | | Immediate Centrifugation | | 15' Incubation 37° C. | | Anti-IgG Serum | |
| Treatment | None | R & A | None | R & A | None | R & A | None | R & A | None | R & A | None | R & A |
| Titer* | 2 | 256+ | 16+ | 2048 | 2048+ | 1024+ | 2+ | 256+ | 16+ | 2048+ | 2048+ | 2048+ |

Anti-C

| | Physiologic Saline | | | | | | Albumin | | | | | |
|---|---|---|---|---|---|---|---|---|---|---|---|---|
| Diluent Test Phase | Immediate Centrifugation | | 15' Incubation Room Temp. | | Anti-IgG Serum | | Immediate Centrifugation | | 30' Incubation 37° C. | | Anti-IgG Serum | |
| Treatment | None | R & A | None | R & A | None | R & A | None | R & A | None | R & A | None | R & A |
| Titer* | <1 | 1 | <1 | 8+ | 32+ | 32+ | 64 | 2 | 128 | 256 | 256+ | 512 |

| | Low Ionic Strength Solution (LISS) of Low and Messeter | | | | | | | | | | | |
|---|---|---|---|---|---|---|---|---|---|---|---|---|
| Diluent Test Phase | Immediate Centrifugation | | 10' Incubation Room Temp. | | Anti-IgG Serum | | Immediate Centrifugation | | 15' Incubation 37° C. | | Anti-IgG Serum | |
| Treatment | None | R & A | None | R & A | None | R & A | None | R & A | None | R & A | None | R & A |
| Titer* | <1 | 32 | <1 | 32 | 256+ | 512+ | <1 | 32 | 4 | 32+ | 128+ | 256 |

| | Low Ionic Strength Medium (LISM) of Example I | | | | | | | | | | | |
|---|---|---|---|---|---|---|---|---|---|---|---|---|
| Diluent Test Phase | Immediate Centrifugation | | 10' Incubation Room Temp. | | Anti-IgG Serum | | Immediate Centrifugation | | 15' Incubation 37° C. | | Anti-IgG Serum | |
| Treatment | None | R & A | None | R & A | None | R & A | None | R & A | None | R & A | None | R & A |
| Titer* | <1 | 16+ | 8+ | 128 | 256+ | 256+ | <1 | 16+ | 64+ | 256+ | 512+ | 256+ |

Anti-c̄

| Physiologic Saline | Albumin |
|---|---|

TABLE IV-continued

| Diluent Test Phase | Immediate Centrifugation | | 15' Incubation Room Temp. | | Anti-IgG Serum | | Immediate Centrifugation | | 30' Incubation 37° C. | | Anti-IgG Serum | |
| --- | --- | --- | --- | --- | --- | --- | --- | --- | --- | --- | --- | --- |
| Treatment | None | R & A | None | R & A | None | R & A | None | R & A | None | R & A | None | R & A |
| Titer* | <1 | 4+ | <1 | 16+ | 128+ | 128 | 128 | 8+ | 512+ | 128 | 1024 | 2048+ |

| Low Ionic Strength Solution (LISS) of Low and Messeter |||||||||||||
| --- | --- | --- | --- | --- | --- | --- | --- | --- | --- | --- | --- | --- |
| Diluent Test Phase | Immediate Centrifugation | | 10' Incubation Room Temp. | | Anti-IgG Serum | | Immediate Centrifugation | | 15' Incubation 37° C. | | Anti-IgG Serum | |
| Treatment | None | R & A | None | R & A | None | R & A | None | R & A | None | R & A | None | R & A |
| Titer* | 1+ | 8+ | 1+ | 32+ | 512 | 512+ | 1+ | 8+ | 4 | 64+ | 512+ | 512+ |

| Low Ionic Strength Medium (LISM) of Example I |||||||||||||
| --- | --- | --- | --- | --- | --- | --- | --- | --- | --- | --- | --- | --- |
| Diluent Test Phase | Immediate Centrifugation | | 10' Incubation Room Temp. | | Anti-IgG Serum | | Immediate Centrifugation | | 15' Incubation 37° C. | | Anti-IgG Serum | |
| Treatment | None | R & A | None | R & A | None | R & A | None | R & A | None | R & A | None | R & A |
| Titer* | 4 | 32 | 8+ | 128 | 512 | 512+ | 4 | 32 | 8+ | 512+ | 2048+ | 1024+ |

If the results obtained with a single antibody preparation diluted in physiologic saline are compared with those diluted in LISM, one sees that the LISM had a significant potentiating effect on both the untreated and the reduced and alkylated antibody. In this case, the potentiation carried through to the antiglobulin phase. A similar but lesser potentiation was exhibited in the low ionic strength solution (LISS). In all cases (excluding the antiglobulin results, which were generally equivalent), the titers achieved with the reduced and alkylated antibody in LISS or LISM were significantly higher than those of the untreated antibody in the same diluent.

Example VII demonstrates that the potentiating effect of reduction and alkylation, or that of either low ionic strength diluent alone, was insufficient to account for the observed potentiation of the invention described herein. Rather, a synergistic effect is clearly at work, requiring both the reduction and alkylation of the antibody and its dilution in low ionic strength diluent such as that described in Example I.

It is claimed:

1. An antiserum for immunohematologic agglutination reactions comprising an erythrocyte-agglutinating amount of a chemically reduced IgG antibody dissolved in a low ionic strength medium containing sufficient salt of an alkali or alkaline earth metal to provide an ionic strength equivalent to about a 0.01 molar to about a 0.10 molar solution of sodium chloride; sufficient organic solute to provide an osmolality of from about 150 mOsm per kg. H₂O, to about 450 mOsm per kg. H₂O and a pH of from about 6.0 to about 8.0.

2. The antiserum of claim 1, wherein the reduced IgG antibody is obtained by chemically reducing an IgG antibody derived from human serum.

3. The antiserum of claim 2, wherein the IgG antibody is derived from about 0.5 to about 3 parts by volume of human serum for about 10 parts by volume of low ionic strength medium.

4. The antiserum of claim 2, wherein the IgG antibody is derived from about 1 to about 2 parts by volume of human serum for about 10 parts by volume of low ionic strength medium.

5. The antiserum of claim 1, 3 or 4 wherein said chemically reduced IgG antibody is alkylated by an alkylating amount of an alkylating agent.

6. The antiserum of claim 5, wherein the alkylating agent is iodoacetamide or iodacetic acid.

7. The antiserum of claim 5, wherein said IgG antibody is an antibody to Rh blood group antigens.

8. The antiserum of claim 7 wherein the IgG antibody is anti-D.

9. The antiserum of claim 7 wherein the IgG antibody is anti-C.

10. The antiserum of claim 7 wherein the IgG antibody is anti-E.

11. The antiserum of claim 7 wherein the IgG antibody is anti-c̄.

12. The antiserum of claim 7 wherein the IgG antibody is anti-ē.

13. The antiserum of claim 5, wherein said IgG antibody is an antibody to Lutheran blood group antigens.

14. The antiserum of claim 5, wherein said IgG antibody is an antibody to Kell blood group antigens.

15. The antiserum of claim 5, wherein said IgG antibody is an antibody to Duffy blood group antigens.

16. The antiserum of claim 5, wherein said IgG antibody is an antibody to Kidd blood group antigens.

17. The antiserum of claim 5, wherein said IgG antibody is an antibody to MNS blood group antigens.

18. The antiserum of claim 5 further comprising gelatin, wherein the product of the gelatin Bloom rating times the concentration of gelatin in weight percent is from about 40 to about 150.

19. The antiserum of claim 18, further comprising albumin in a concentration from about 3.0 weight percent to about 7.0 weight percent.

20. The antiserum of claim 19 wherein the albumin is substantially salt-free bovine serum albumin.

21. The antiserum of claim 5 wherein the osmolality is from about 250 mOsm/kg. H₂O to about 400 mOsm/kg. H₂O, and the salt is sodium chloride, potassium chloride, or sodium azide.

22. The antiserum of claim 18 wherein the osmolality is from about 250 mOsm/kg. H₂O to about 400 mOsm/kg. H₂O, the product of the gelatin Bloom rating times the gelatin concentration in weight percent is from about 45 to about 90, and the salt is sodium chloride, potassium chloride, or sodium azide.

23. The antiserum of claim 18 wherein the organic solute is an amino acid, a sugar, or a water soluble alcohol, and the gelatin has a Bloom rating of from about 100 to about 275.

24. A method of preparing the antiserum of claim 1, comprising reacting a serum containing an IgG antibody with a disulfide reducing compound under antibody-reducing conditions to form a reduced IgG antibody; dissolving the reduced IgG antibody in a low ionic strength medium containing sufficient salt of an alkali or alkaline earth metal to provide an ionic strength equivalent to about a 0.01 molar to about a 0.10 molar solution of sodium chloride; sufficient organic solute to provide an osmolality of from about 150 mOsm per kg. H$_2$O, to about 450 mOsm per kg. H$_2$O and a pH of from about 6.0 to about 8.0.

25. The method of claim 24 wherein said antibody reducing conditions include incubating said serum and said disulfide reducing compound at room temperature for about 30–90 minutes.

26. The method of claim 24 wherein said disulfide reducing compound is dithiothreitol, dithioerythritol or mercaptoethanol.

27. The method of claim 24 further comprising alkylating the reduced IgG antibody by adding an alkalating amount of an alkylating agent to the serum under alkylating conditions.

28. The method of claim 27 wherein said alkylating agent iodoacetamide or iodoacetic acid is added at a concentration of 0.002–0.5 mmoles of alkylating agent per ml. of serum.

29. A method of using antiserum of claim 1, comprising combining said antiserum with a patient's erythrocytes under erythrocyte-agglutinating conditions and determining whether or not said erythrocytes agglutinate.

* * * * *